United States Patent [19]

Lilja et al.

[11] Patent Number: 4,654,197
[45] Date of Patent: Mar. 31, 1987

[54] CUVETTE FOR SAMPLING AND ANALYSIS

[75] Inventors: Jan E. Lilja, Kristianstad; Sven E. L. Nilsson, Helsingborg, both of Sweden

[73] Assignee: Aktiebolaget Leo, Helsingborg, Sweden

[21] Appl. No.: 660,466

[22] Filed: Oct. 12, 1984

[30] Foreign Application Priority Data

Oct. 18, 1983 [SE] Sweden .................................. 8305704

[51] Int. Cl.⁴ ..................... G01N 21/78; G01N 27/28; G01N 33/52
[52] U.S. Cl. ..................................... 422/56; 204/403; 422/58; 422/61; 435/810
[58] Field of Search .................... 422/58, 100, 102, 61, 422/56, 57; 436/165, 172, 166, 178; 356/246; 204/403; 435/810

[56] References Cited

U.S. PATENT DOCUMENTS

| 3,420,205 | 1/1969 | Morison | 422/56 X |
|---|---|---|---|
| 3,787,291 | 1/1974 | Deuringer et al. | 204/403 X |
| 3,865,548 | 2/1975 | Padawer | 422/61 X |
| 3,904,373 | 9/1975 | Harper | 436/166 X |
| 4,003,707 | 1/1977 | Lubbers et al. | 436/172 |
| 4,008,448 | 5/1978 | Lilja et al. | 356/246 X |
| 4,042,335 | 8/1977 | Clement | 422/56 |
| 4,200,110 | 4/1980 | Peterson et al. | 436/163 X |
| 4,233,029 | 11/1980 | Columbus | 422/55 X |
| 4,234,316 | 11/1980 | Hevey | 436/166 |
| 4,269,804 | 5/1981 | Kring | 422/61 X |
| 4,323,536 | 4/1982 | Columbus | 422/58 X |
| 4,387,164 | 6/1983 | Hevey et al. | 436/166 X |
| 4,418,148 | 11/1983 | Oberhardt | 204/403 X |

FOREIGN PATENT DOCUMENTS

| 0078225 | 5/1983 | European Pat. Off. | 436/166 |
|---|---|---|---|
| 2039039 | 7/1980 | United Kingdom | 436/166 |

OTHER PUBLICATIONS

Romette et al., Clinica Chimica Acta, 95 (1979), 249-253.
Mascini et al., Analytical Chemistry, vol. 49, No. 6, May 1977, pp. 795-798.
Vadgama, Journal of Medical Engineering & Technology, vol. 5, No. 6, Nov. 1981, pp. 293-298.

Primary Examiner—Arnold Turk
Attorney, Agent, or Firm—Burgess, Ryan & Wayne

[57] ABSTRACT

Disposable cuvette for essentially simultaneous sampling of a fluid and analyzing the sample. The new cuvette comprises a body member having at least one cavity defined by surrounding walls, into which cavity the sample is permitted to enter by capillary force through an inlet communicating said cavity with the exterior of the body member. According to the invention, the cuvette is characterized in that at least a portion of the walls facing the cavity consists of a semipermeable membrane, optionally with an integrated electrode and/or sensor system, and that at least one reagent or reagent system is incorporated in the cuvette.

12 Claims, 10 Drawing Figures

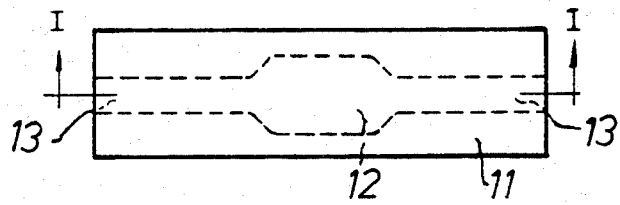
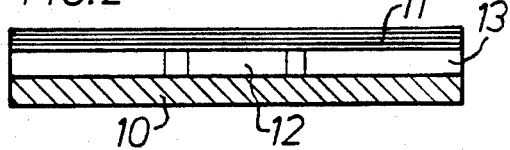
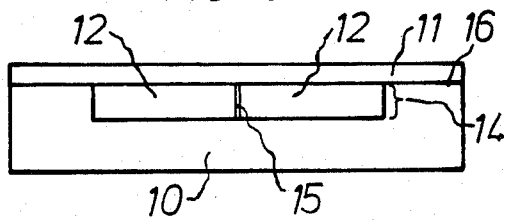
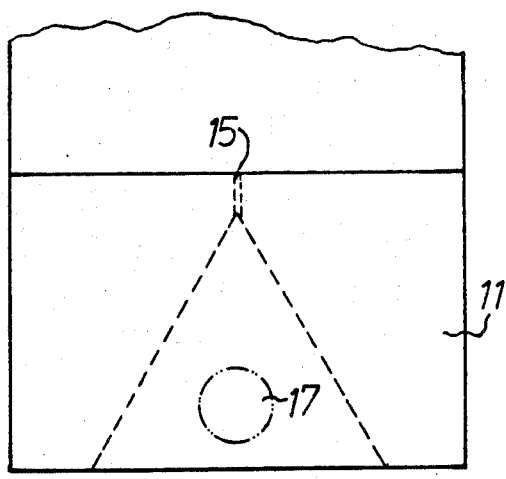

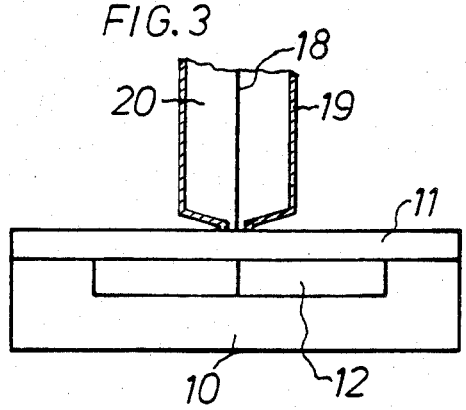
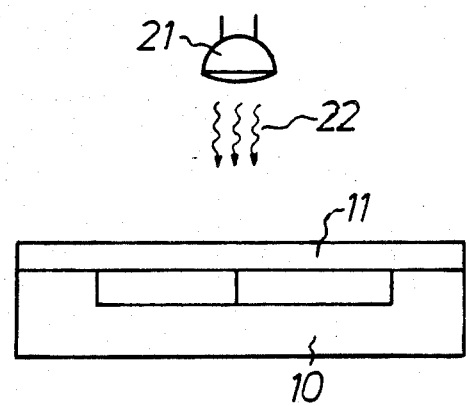
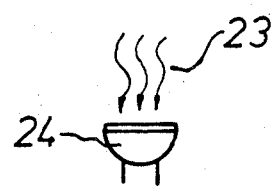

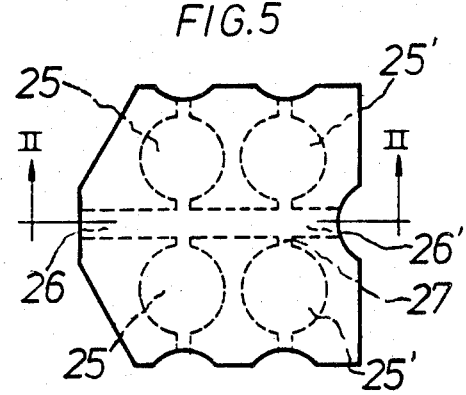
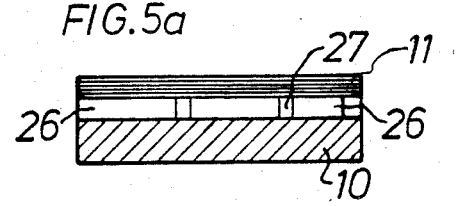
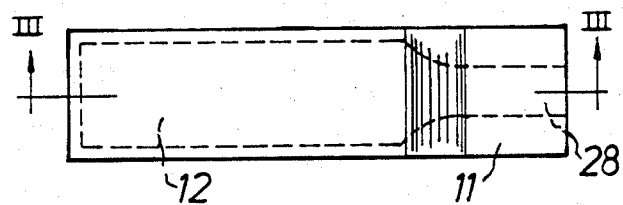
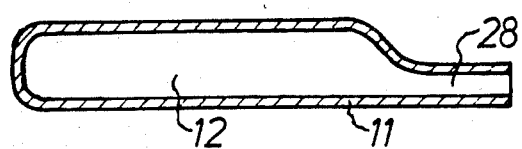

CUVETTE FOR SAMPLING AND ANALYSIS

The present invention concerns a disposable cuvette for essentially simultaneous sampling of a fluid and analyzing the sample.

A cuvette for sampling a fluid, mixing the sample with a reagent and directly making optical analyses of the sample mixed with the reagent is previously known from U.S. Pat. No. 4,088,448. This cuvette comprises a body member including two planar surfaces defining an optical path and placed at a predetermined distance from one another to determine the optical path length and to define a cavity having an inlet communicating said cavity with the exterior of the body member. The cavity has a predetermined fixed volume, and the predetermined distance permits the sample to enter the cavity by capillary force. Furthermore, a reagent is coated on the cavity surface.

This known cuvette has serveral advantages when compared with conventionally used devices. It permits sampling of a liquid, mixing and chemically reacting it with a suitable reagent e.g. colour development in the same vessel as the one used for the subsequent measurement. The cuvette disclosed in U.S. Pat. No. 4,088,448 thus simplifies the sampling procedure, reduces the number of utensils and—in most cases, depending on the type of analysis—considerably improves the accuracy of analysis by making the analyzing procedure independent of the operating technique of the operator making the analysis.

The present invention concerns an improvement of this known cuvette.

To this end, there has been developed a disposable cuvette for essentially simultaneous sampling of a fluid and analyzing the sample, comprising a body member having at least one cavity defined by surrounding walls, into which cavity a sample is permitted to enter by capillary force through an inlet communicating said cavity with the exterior of said body member, the cuvette being characterized in that at least a portion of the walls facing the cavity consists of a semipermeable membrane, optionally with an integrated electrode and/or sensor system, and that at least one reagent or reagent system is incorporated in the cuvette.

One advantage of the improved cuvette is that it can be used for other types of measurements than optical analyses, which makes it applicable to analyses within a much broader range than the cuvette according to U.S. Pat. No. 4,088,448. Thus, according to the present invention, the measurement can be carried out by using different electrodes, the surfaces of which are pressed against the exterior surface of the semipermeable membrane. Furthermore, optical instruments may be used. Within the scope of the present invention are also electrode or sensor systems integrated with, i.e. applied on or incorporated in, the semipermeable membrane material.

Another very important advantage as compared with the previously known cuvette is that the use of membranes makes it possible to separate sample media from reagent media, and interferences originating from substances, unsuitable pH; unsuitable redox environment etc. can be avoided. Thus, two or more reaction systems, which are incompatible, may be included in the new cuvette, as the semipermeable membrane acts as a barrier which prevents a component, e.g. a reagent contained in the cavity from entering and disturbing the reaction(s) in the membrane(s), and vice versa. This second advantage makes the field of application for the present cuvette even broader and useful for a wide variety of different analyses.

Thus, the additional advantages according to the present invention emanate from the use of the semipermeable membrane and the possibility of combining this membrane with external or internal electrodes.

Analyses based on the use of semipermeable membranes and electrodes are known in the art. However, using known techniques, difficulties are encountered in the handling of the sample, electrodes which often are sensitive to contamination, may be contaminated, evaporation of the sample may occur, and the sample may be subjected to the influence of different types of gases, such as the oxygen of the air. All these problems can be avoided by using the cuvette according to the present invention.

According to the present invention, the body member may consist of glass or polymeric material. It is also quite possible to make the whole body member or one wall thereof of the semipermeable material which in this case preferably should be self-supporting. If not essentially self-supporting, the membrane could be used as a coating on the surface of the body member facing the cavity. The reagent, if any, coated on at least a portion of the body (body member) surface facing the cavity may be deposited by evaporation, freeze-drying, spraying or screen-printing, as known in the art.

The semipermeable membrane may be in the form of one separate membrane layer or two or more separate layers joined to each other to form a composite membrane. The various reagents may be coated on the membrane surface facing the cavity and applied thereto by evaporation, freeze-drying, spraying or screenprinting, etc. It is also possible to have the reagents deposited as a layer on separate surfaces of the membrane in such a way that this layer becomes an intermediate layer in the finished composite membrane. One or more such layers may be present. The semipermeable membrane may also be prepared in such a manner that the reagent or reagents are dispersed or dissolved throughout the whole membrane or one or more layers thereof. Another possibility is to prepare the membrane material in such a manner that the reagent molecules are covalently bound to the polymer molecules of the semipermeable membrane.

The semipermeable membrane material is chosen in dependence on the kind of analysis to be performed and may be determined by a person skilled in the art. The membrane material might be hydrophilic or hydrophobic. Examples of different material which can be used according to the present invention are Teflon ®, silicon rubber, polyacrylates, polyvinyls, collagen and even crosslinked enzymes, etc.. Various substances could be incorporated in the membrane to give special selective properties, to perform a chemical reaction, etc. Including specific crown ethers in a polyvinyl membrane gives a membrane with selective properties for alkaline ions. Including glucose oxidase in a membrane makes it possible to measure glucose by the production of hydrogen peroxide or the decrease in oxygen concentration.

The membrane may selectively permit penetration of only or essentially the substance/ion, which is relevant/interesting, and which can be detected by, for example, an electrode on the external surface of the membrane. Furthermore, the membrane may function as a discriminator in which only molecules/ions below a certain size can move freely.

To perform measurements with electrodes on or in the improved cuvette, the membrane acts as a semipermeable barrier (with or without selective properties) which prevents the electrodes from being contaminated by the sample medium and/or the reagent. The membrane could participate in a chemical reaction through incorporated reagents and/or selectively permit free passage for the substances to be determined at the electrode.

The electrode to be used according to the present invention may be a conventional potentiometric, i.e. ion-selective or amperometric electrode which, together with the semipermeable membrane of the cuvette, functions as an enzyme electrode or biosensor of the type described in e.g. P. Vadgama, Journal of Medical Engineering & Technology, Vol. 5, No. 6, 1981, 293–298.

Examples of electrodes to be used with the membrane cuvette of the present invention are conventional electrodes, such as a glass electrode (pH), a platinum, gold, or carbon electrode, and other more exclusive electrodes, such as solid state devices of the type CHEMFET or ISFET with their associated electronic parts.

An example of a platinum/silver-silver chloride electrode system together with a composite membrane for determining glucose by amperometric measurement of consumed oxygen is given in a paper by Jean-Louis Romtte, B. Frommment & D. Thomas (Clin. Chim. Acta, 95 (1979) 249–253).

An example of glass electrode application together with a composite membrane for determining urea by pH-measurement of produced ammonia is disclosed in a paper by M. Mascini and G.G. Guilbault (Anal. Chem., Vol. 49, No. 6, May 1977, 795–798).

As regards optical analyses to be performed with the present cuvette, there are two main possibilities:

(A) the colour develops in the cavity;
(B) the colour develops within the membrane.

In (A), the two main surfaces of the cavity must have a predetermined or a determinable distance between one another to make it possible to determine the optical path length. The determinable distance may be obtained by applying an external force to the surface of an essentially elastic membrane until the movement of the membrane is stopped against a spacer of predetermined thickness inserted in the cavity.

In (B), the colour developing part (layer) of the membrane or the entire membrane must be of a predetermined thickness to accomplish a determined optical path length.

A practical example of (B) is a cuvette designed to perform an analysis of urea in serum or urine. The cavity contains urease and an alkaline buffer system in dry form which, when dissolved in the sample medium, give free ammonia from urea, and the membrane incorporates an indicator (=a reagent) for ammonia. The membrane is manufactured from a polymer, the hydrophobicity of which is sufficienty high to prevent the alkaline buffer from interfering with the indicator, but is permeable to ammonia. The indicator is a solvent soluble pH-indicator with an indicator interval within the acid range.

Different approaches to the analyses may be made by using different types of electrodes, different types of membranes and different reaction routes, as recognized by a person skilled in the art.

The invention will be described in more detail below, reference being had to the accompanying drawings which illustrate schematically and on a large scale a number of embodiments. In the drawings:

FIG. 1 shows an elevational view of a measuring cuvette according to the invention.

FIG. 2 shows a section on line I—I in FIG. 1;

FIG. 2a shows an elevational view of a modified embodiment of the cuvette;

FIG. 2b shows a view of top plan view of the cuvette FIG. 2a;

FIG. 3 shows an elevational view of the cuvette according to FIGS. 2 and 2a in contact with a measuring electrode;

FIG. 4 shows an elevational view of the cuvette according to FIGS. 2 and 2a adapted for optical measurement;

FIG. 5 shows a plan view of an embodiment in which the cuvette has parallel-connected cavities;

FIG. 5a shows a section on line II—II of FIG. 5;

FIG. 6 shows a plan view of a further modified embodiment of the cuvette;

FIG. 6a shows a section on line III—III of FIG. 6.

The cuvette illustrated in FIGS. 1 and 1a comprises a body wall 10 of glass or polymeric material, and a body wall 11 of semipermeable membrane material. The walls define a cavity 12 which is intended to accommodate a liquid sample and the dimension of which is such that it can be filled by capillary force. Two channels 13 extend from opposite sides of the cuvette and open into the cavity 12. Thus, a sample can here be drawn straight through the cuvette, which may be advantageous in certain cases. The cavity 12 might be supplied with a reagent (that is an agent to react with the sample drawn into said cavity) by evaporation, freeze-drying, spraying, screen-printing or in another suitable manner according to the manner in which the cuvette is manufactured.

The wall 11 of semipermeable membrane material may be manufactured in such a manner that a reagent system is incorporated in the memebrane, e.g. dispersed or dissolved therein. It is also possible to manufacture the membrane in such a way that the components (molecules) of the reagent system are covalently bound to the polymers constituting the membane material. Another possibility is to build up a semipermeable membrane of two or more layers and apply the reagent systems as intermediate layers between two adjacent membrane layers. One or more such layers and intermediate layers may be present. All types of combinations of incorporation of the reagent system apparent to those skilled in the art fall within the scope of the present invention.

In FIG. 2a, 10 is a body wall of polymeric supporting material. 11 is a semipermeable membrane optically composed of several layers. 12 is the cavity accommodating the sample. Elevations 14 determine the optical path length. When the sample is drawn into the cavity 12, air is pressed out through the slit 15. The body wall 10 and the semipermeable membrane 11 are joined together (welded or glued) along the joint 16. The area 17 indicates a suitable measuring zone.

In FIG. 3 a measuring electrode is brought into contact with the semipermeable membrane 11 in the cuvette disclosed in FIGS. 2a and 2b. In this special embodiment, the electrode consists of a platinum electrode 18 and a reference silver/silver chloride electrode 19. 20 designates the glass body surrounding the platinum electrode 18.

In FIG. 4 cuvette of the FIGS. 2a and 2b is adapted for optical measuring. Thus, 21 here designates a light source e.g. monochromatic light. 22 indicates the light path towards the cuvette. 23 indicates the light path of unabsorbed light after the cuvette, and 24 is an optical detector.

The cuvette as shown in FIG. 5 has four parallel-connected cavities 25, 25' which are connected to a common channel, 26' by branch channels 27 which continue on the opposite side of the cavities and open into the atmosphere to prevent air inclusions in the cavities when samples are drawn thereinto. Different reactive systems may be included in different cavities and/or the membrane material defining the whole or part of the cavity.

FIG. 5a shows a section of the cuvette according to FIG. 5 along line II—II.

The embodiment of the present invention according to FIGS. 6 and 6a consists of elastic semipermeable material. The inlet channel 28 communicates the exterior of the cuvette with the cavity 12.

While the invention has been described with reference to preferred embodiments thereof, it will be understood by those skilled in the art that various changes in form and details may be made without departing from the spirit and scope of the invention. Many alternative container designs can be conceived which give the advantageous results herein disclosed.

Further, it is obvious that any analytical procedure can be adapted to the invention herein disclosed. The cuvette is particularly suitable for routine blood chemistry, such as glucose, blood urea nitrogen, albumin, bilirubin, total protein, etc., and numerous other analytical tests.

Accordingly, all substitutions, additions and modifications to which the present invention is readily susceptible, without departing from the spirit and scope of this disclosure, are considered part of the present invention.

What we claim and desire to secure by Letters Patent is:

1. A disposable cuvette for simultaneously sampling a fluid and analyzing the sampled fluid, comprising:
    a body member having an exterior and at least one cavity defined by surrounding walls,
    an inlet in said walls communicating said cavity with the exterior of the body member and through which said sampled fluid can enter said cavity by capillary forces, at least one of the walls including a semipermeable membrane, said semipermeable membrane having one surface defining a portion of said cavity and an opposite surface forming an external surface of said cuvette, said semipermeable membrane having a predetermined porosity and thereby functioning as a discriminator to permit entry only of molecules/ions up to a certain size, and at least one reagent incorporated in the cuvette in contact with said semipermeable membrane.

2. Cuvette according to claim 1, wherein said semipermeable membrane includes a polymeric material, and molecules of the at least one reagent are covalently bound to the polymers of the semipermeable membrane.

3. Cuvette accoridng to claim 1, wherein said at least one reagent is coated on at least a portion of a surface of said semipermeable membrane facing the cavity.

4. Cuvette according to claim 1, wherein said surrounding walls of said cavity are defined by two spaced planar surfaces, and said two planar surfaces of the cavity define an optical path length.

5. Cuvette according to claim 1, wherein the semipermeable membrane has a predetermined fixed thickness defining an optical path length.

6. Cuvette according to claim 1, further including sensor means applied on the semipermeable membrane for analyzing a sampled fluid.

7. Cuvette according to claim 1, further including sensor means incorporated in the semipermeable membrane for analyzing a sampled fluid.

8. Cuvette according to claim 1, wherein the semipermeable membrane comprises at least one membrane layer.

9. Cuvette according to claim 8, wherein at least one reagent is in contact with at least one membrane layer of the semipermeable membrane.

10. Cuvette according to claim 9, wherein said at least one reagent is dispersed in at least one layer of said semipermeable membrane.

11. Cuvette according to claim 9, wherein said at least one reagent is dissovled in at least one layer of said semipermeable membrane.

12. Cuvette according to claim 9, wherein said at least one reagent is located on said semipermeable membrane.

* * * * *